US012807574B2

(12) United States Patent
Dale et al.

(10) Patent No.: US 12,807,574 B2
(45) Date of Patent: Nov. 24, 2026

(54) HERBICIDAL DERIVATIVES

(71) Applicant: SYNGENTA CROP PROTECTION AG, Basel (CH)

(72) Inventors: Suzanna Jane Dale, Bracknell (GB); Christopher James Martin, Bracknell (GB); David Burns, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 509 days.

(21) Appl. No.: 18/255,416

(22) PCT Filed: Nov. 26, 2021

(86) PCT No.: PCT/EP2021/083129
§ 371 (c)(1),
(2) Date: Jun. 1, 2023

(87) PCT Pub. No.: WO2022/117446
PCT Pub. Date: Jun. 9, 2022

(65) Prior Publication Data

US 2024/0002342 A1 Jan. 4, 2024

(30) Foreign Application Priority Data

Dec. 2, 2020 (GB) ...................................... 2018996

(51) Int. Cl.

| | |
|---|---|
| ***C07D 213/80*** | (2006.01) |
| ***A01N 43/40*** | (2006.01) |
| ***A01P 13/00*** | (2006.01) |

(52) U.S. Cl.
CPC ............ *C07D 213/80* (2013.01); *A01P 13/00* (2021.08)

(58) Field of Classification Search
None
See application file for complete search history.

(56) References Cited

U.S. PATENT DOCUMENTS

| | | | | | |
|---|---|---|---|---|---|
| 4,714,492 | A | * | 12/1987 | Carlson .................. | A01H 1/026 546/316 |
| 4,936,904 | A | * | 6/1990 | Carlson .................. | A01H 1/026 546/316 |
| 4,964,896 | A | * | 10/1990 | Carlson .................. | A01H 1/023 546/288 |

FOREIGN PATENT DOCUMENTS

| | | | | | |
|---|---|---|---|---|---|
| EP | 0040082 | A1 | | 11/1981 | |
| EP | 0127313 | A1 | | 12/1984 | |
| EP | 0239391 | A2 | | 9/1987 | |
| GB | 2182931 | A | * | 5/1987 | ............. A01N 43/40 |
| JP | S62167708 | A | | 7/1987 | |
| JP | S62167709 | A | | 7/1987 | |
| JP | S62167712 | A | * | 7/1987 | |
| JP | S62167718 | A | | 7/1987 | |
| JP | S62-192305 | A | | 8/1987 | |
| JP | S62249973 | A | | 10/1987 | |
| JP | S63-14770 | A | | 1/1988 | |

OTHER PUBLICATIONS

Koyanagi et al. (Ch 2: Bioisosterism . . . , from Baker et al. Synthesis and Chem. of Agrochem. IV, ACS, 1995, p. 15-24). (Year: 1995).*

Patani et al. (Chem. Rev., 1996, 96, 3147-3176) (Year: 1996).*

UKIPO; App. No. GB 2018996.5; Search Report under Section 17 dated Mar. 24, 2021; pp. 1-4.

WIPO; App. No. PCT/EP2021/083129; International Search Report and Written Opinion mailed Mar. 7, 2022; pp. 1-9.

First Office Action and Search Report for Chinese Application No. 202180081274.6, mailed Nov. 19, 2025, with English translation. 14 pages.

* cited by examiner

*Primary Examiner* — Erin E Hirt
(74) *Attorney, Agent, or Firm* — BakerHostetler; Toni-Junell Herbert

(57) ABSTRACT

Compounds of the Formula (I) wherein the substituents are as defined in claim 1. The invention further relates to herbicidal compositions which comprise a compound of Formula (I) and to the use of compounds of Formula (I) for controlling weeds, in particular in crops of useful plants.

(I)

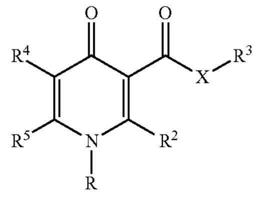

21 Claims, No Drawings

HERBICIDAL DERIVATIVES

CROSS-REFERENCE TO RELATED APPLICATIONS

This application is a U.S. National Stage Application, filed under 35 U.S.C. § 371, of International Application No. PCT/EP2021/083129, filed Nov. 26, 2021, which claims priority to GB 2018996.5, filed Dec. 2, 2020, the entire contents of which are incorporated by reference herein.

The present invention relates to herbicidal pyridone derivatives, e.g., as active ingredients, which have herbicidal activity. The invention also relates to agrochemical compositions which comprise at least one of the pyridone derivatives, to processes of preparation of these compounds and to uses of the pyridone derivatives or compositions in agriculture or horticulture for controlling weeds, in particular in crops of useful plants.

EP0239391, EP0127313, EP0040082, and GB2182931 describe pyridone derivatives as herbicidal agents.

According to the present invention, there is provided a compound of Formula (I):

(I)

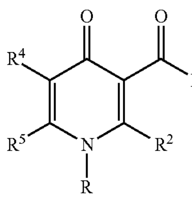

wherein

X is O, $NR^6$, or S;

$R^1$ is $C_1$-$C_6$alkyl;

$R^2$ is phenyl, or heteroaryl, wherein the heteroaryl moiety is a 5- or 6-membered aromatic ring which comprises 1, 2, 3 or 4 heteroatoms individually selected from N, O and S, and wherein each phenyl and heteroaryl moiety may be optionally substituted with 1, 2, 3, or 4 groups, which may be the same or different, represented by $R^7$;

$R^3$ is hydrogen, $C_1$-$C_6$alkyl, N,N-di($C_1$-$C_3$alkyl)amino, $C_1$-$C_6$haloalkyl, $C_3$-$C_6$cycloalkyl, $C_3$-$C_6$cycloalkyl$C_1$-$C_6$alkyl, $C_1$-$C_6$alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties may be optionally substituted with 1, 2, 3 or 4 groups, which may be the same or different, represented by $R^8$;

$R^4$ is cyano, $C_2$-$C_6$alkenyl, $C_2$-$C_6$alkynyl, $C_1$-$C_6$alkoxy$C_2$-$C_6$alkenyl, $C_2$-$C_6$alkenyloxy$C_1$-$C_6$alkyl, $C_1$-$C_6$alkylcarbonyl, or hydroxycarbonyl;

$R^5$ is halogen, $C_1$-$C_4$alkyl, $C_1$-$C_4$alkoxy, $C_1$-$C_4$haloalkyl, or $C_1$-$C_4$alkoxy$C_1$-$C_4$alkyl;

$R^6$ is hydrogen, $C_1$-$C_3$alkyl, or $C_1$-$C_3$alkoxy;

$R^7$ is halogen, $C_1$-$C_3$alkyl, or $C_1$-$C_3$alkoxy;

$R^8$ is halogen, cyano, $C_1$-$C_3$alkyl, or $C_1$-$C_3$alkoxy;

or a salt or an N-oxide thereof.

Surprisingly, it has been found that the novel compounds of Formula (I) have, for practical purposes, a very advantageous level of herbicidal activity.

According to a second aspect of the invention, there is provided an agrochemical composition comprising a herbicidally effective amount of a compound of Formula (I) according to the present invention. Such an agricultural composition may further comprise at least one additional active ingredient and/or an agrochemically-acceptable diluent or carrier.

According to a third aspect of the invention, there is provided a method of controlling weeds at a locus comprising applying to the locus a weed controlling amount of a composition comprising a compound of Formula (I).

According to a fourth aspect of the invention, there is provided the use of a compound of Formula (I) as a herbicide.

Where substituents are indicated as being "optionally substituted", this means that they may or may not carry one or more identical or different substituents, e.g., one, two or three $R^7$ substituents. For example, $C_1$-$C_6$alkyl substituted by 1, 2 or 3 halogens, may include, but not be limited to, —$CH_2Cl$, —$CHCl_2$, —$CCl_3$, —$CH_2F$, —$CHF_2$, —$CF_3$, —$CH_2CF_3$ or —$CF_2CH_3$ groups. As another example, $C_1$-$C_6$alkoxy substituted by 1, 2 or 3 halogens, may include, but not limited to, $CH_2ClO$—, $CHCl_2O$—, $CCl_3O$—, $CH_2FO$—, $CHF_2O$—, $CF_3O$—, $CF_3CH_2O$— or $CH_3CF_2O$— groups.

As used herein, the term "cyano" means a —CN group.

As used herein, the term "halogen" refers to fluorine (fluoro), chlorine (chloro), bromine (bromo) or iodine (iodo).

As used herein, the term "hydroxy" means an —OH group.

As used herein, the term "acetyl" means a —C(O)$CH_3$ group.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. "$C_1$-$C_4$alkyl" and "$C_1$-$C_3$alkyl" are to be construed accordingly. Examples of $C_1$-$C_6$alkyl include, but are not limited to, methyl, ethyl, n-propyl, and the isomers thereof, for example, iso-propyl. A "$C_1$-$C_6$alkylene" group refers to the corresponding definition of $C_1$-$C_6$alkyl, except that such radical is attached to the rest of the molecule by two single bonds. The term "$C_1$-$C_2$alkylene" is to be construed accordingly. Examples of $C_1$-$C_6$alkylene, include, but are not limited to, —$CH_2$—, —$CH_2CH_2$— and —$(CH_2)_3$—.

As used herein, the term "$C_1$-$C_6$haloalkyl" refers a $C_1$-$C_6$alkyl radical as generally defined above substituted by one or more of the same or different halogen atoms. The terms "$C_1$-$C_4$haloalkyl" and "$C_1$-$C_3$haloalkyl", are to be construed accordingly. Examples of $C_1$-$C_6$haloalkyl include, but are not limited to trifluoromethyl.

As used herein, the term "$C_1$-$C_6$alkoxy" refers to a radical of the formula —$OR_a$ where $R_a$ is a $C_1$-$C_6$alkyl radical as generally defined above. The terms "$C_1$-$C_4$alkoxy" and "$C_1$-$C_3$alkoxy" are to be construed accordingly. Examples of $C_1$-$C_6$alkoxy include, but are not limited to, methoxy, ethoxy, 1-methylethoxy (iso-propoxy), and propoxy.

As used herein, the term "$C_2$-$C_6$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. The term "$C_2$-$C_3$alkenyl" is to be construed accordingly. Examples of $C_2$-$C_6$alkenyl include, but are not limited to, ethenyl (vinyl), prop-1-enyl, prop-2-enyl (allyl), but-1-enyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_3$alkynyl" is to be construed accordingly. Examples of $C_2$-$C_6$alkynyl include, but are not limited to, ethynyl, prop-1-ynyl, but-1-ynyl.

As used herein, the term "$C_1$-$C_6$alkoxy$C_1$-$C_6$alkyl" refers to a radical of the formula $R_bOR_a$— wherein $R_b$ is a $C_1$-$C_6$alkyl radical as generally defined above, and $R_a$ is a $C_1$-$C_6$alkylene radical as generally defined above.

As used herein, the term "$C_3$-$C_6$cycloalkyl" refers to a radical which is a monocyclic saturated ring system and which contains 3 to 6 carbon atoms. The terms "$C_3$-$C_5$cycloalkyl" and "$C_3$-$C_4$cycloalkyl" are to be construed accordingly. Examples of $C_3$-$C_6$cycloalkyl include, but are not limited to, cyclopropyl, cyclobutyl, cyclopentyl and cyclohexyl.

As used herein, the term "$C_3$-$C_6$cycloalkyl$C_1$-$C_6$alkyl" refers to a $C_3$-$C_6$cycloalkyl ring attached to the rest of the molecule by a $C_1$-$C_6$alkylene linker as defined above.

As used herein, the term "$C_1$-$C_6$alkoxy$C_2$-$C_6$alkenyl" refers to a radical of the formula $R_bOR_a$— wherein $R_b$ is a $C_1$-$C_6$alkyl radical as generally defined above, and $R_a$ is a $C_1$-$C_6$alkene radical as generally defined above.

As used herein, the term "$C_2$-$C_6$alkenyloxy$C_1$-$C_6$alkyl" refers to a radical of the formula $R_bOR_a$— wherein $R_b$ is a $C_2$-$C_6$alkenyl radical as generally defined above, and $R_a$ is a $C_1$-$C_6$alkylene radical as generally defined above.

As used herein, the term "phenyl$C_1$-$C_3$alkyl" refers to a phenyl ring attached to the rest of the molecule by a $C_1$-$C_3$alkylene linker as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur.

Examples of heteroaryl include, but are not limited to, furanyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "$C_1$-$C_6$alkylcarbonyl" refers to a radical of the formula —C(O)$R_a$, where $R_a$ is a $C_1$-$C_6$alkyl radical as generally defined above.

As used herein, the term "hydroxycarbonyl" or "carboxy" refers to a radical of the formula —C(O)OH, As used herein, the term "N,N-di($C_1$-$C_3$alkyl)amino" refers to a radical of the formula —N($R_a$)($R_b$), wherein $R_a$ and $R_b$ are each individually a $C_1$-$C_3$alkyl radical as generally defined above.

The presence of one or more possible stereogenic elements in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form. Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents X, $R^1$, $R^2$, $R^3$, $R^4$, $R^5$, $R^6$, $R^7$, $R^8$, and $R^9$ with reference to compounds of formula (I). For any one of these substituents, any of the definitions given below may be combined with any definition of any other substituent given below or elsewhere in this document.

X is O, $NR^6$, or S. In one set of embodiments X is O. In another set of embodiments, X is $NR^6$. In a further set of embodiments, X is S.

$R^1$ is $C_1$-$C_6$alkyl. Preferably, $R^1$ is $C_1$-$C_4$alkyl. More preferably, $R^1$ is $C_1$-$C_3$alkyl. More preferably still, $R^1$ is methyl, ethyl, n-propyl, or isopropyl. Even more preferably, $R^1$ is methyl or ethyl. Most preferably, $R^1$ is ethyl.

$R^2$ is phenyl or heteroaryl, wherein the heteroaryl moiety is a 5- or 6-membered aromatic ring which comprises 1, 2, 3 or 4 heteroatoms individually selected from N, O and S, and wherein each phenyl and heteroaryl moiety may be optionally substituted with 1, 2, 3, or 4 groups, which may be the same or different, represented by $R^7$.

Preferably, $R^2$ is phenyl or heteroaryl, wherein the heteroaryl moiety is a 5- or 6-membered aromatic ring which comprises 1, 2, or 3 heteroatoms individually selected from N, O and S, and wherein each phenyl and heteroaryl moiety may be optionally substituted with 1, 2, or 3 groups, which may be the same or different, represented by $R^7$.

More preferably, $R^2$ is phenyl or heteroaryl, wherein the heteroaryl moiety is a 5- or 6-membered aromatic ring which comprises 1 or 2 heteroatoms individually selected from N and O, and wherein each phenyl and heteroaryl moiety may be optionally substituted with 1, 2, or 3 groups, which may be the same or different, represented by $R^7$.

More preferably still, $R^2$ is phenyl or heteroaryl, wherein the heteroaryl moiety is a 5- or 6-membered aromatic ring which comprises 1 or 2 heteroatoms individually selected from N and O, and wherein each phenyl and heteroaryl moiety may be optionally substituted with 1 or 2 groups, which may be the same or different, represented by $R^7$.

Even more preferably, $R^2$ is phenyl optionally substituted with 1 or 2 groups, which may be the same or different, represented by $R^7$. In one set of embodiments, $R^2$ is 3,4-dichlorophenyl.

$R^3$ is hydrogen, $C_1$-$C_6$alkyl, N,N-di($C_1$-$C_3$alkyl)amino, $C_1$-$C_6$haloalkyl, $C_3$-$C_6$cycloalkyl, $C_3$-$C_6$cycloalkyl$C_1$-$C_6$alkyl, $C_1$-$C_6$alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties may be optionally substituted with 1, 2, 3 or 4 groups, which may be the same or different, represented by $R^8$.

Preferably, $R^3$ is hydrogen, $C_1$-$C_6$alkyl, N,N-di($C_1$-$C_3$alkyl)amino, $C_1$-$C_4$haloalkyl, $C_3$-$C_6$cycloalkyl, $C_3$-$C_6$cycloalkyl$C_1$-$C_3$alkyl, $C_1$-$C_6$alkoxy$C_1$-$C_3$alkyl, $C_2$-$C_4$alkenyl, $C_2$-$C_4$alkynyl, phenyl, or phenyl$C_1$-$C_2$alkyl, wherein the phenyl moieties may be optionally substituted with 1, 2, or 3 groups, which may be the same or different, represented by $R^8$.

More preferably, $R^3$ is hydrogen, $C_1$-$C_6$alkyl, N,N-di($C_1$-$C_3$alkyl)amino, $C_1$-$C_3$haloalkyl, $C_3$-$C_6$cycloalkyl, $C_3$-$C_6$cycloalkyl$C_1$-$C_3$alkyl, $C_1$-$C_4$alkoxy$C_1$-$C_2$alkyl, $C_2$-$C_3$alkenyl, $C_2$-$C_3$alkynyl, phenyl, or phenyl$C_1$-$C_2$alkyl, wherein the phenyl moieties may be optionally substituted with 1, 2, or 3 groups, which may be the same or different, represented by $R^8$.

More preferably still, $R^3$ is hydrogen, $C_1$-$C_6$alkyl, or N,N-di($C_1$-$C_3$alkyl)amino, $C_1$-$C_3$haloalkyl, $C_3$-$C_6$cycloalkyl, $C_3$-$C_6$cycloalkyl$C_1$-$C_3$alkyl, $C_1$-$C_4$alkoxy$C_1$-$C_2$alkyl, $C_2$-$C_3$alkenyl, $C_2$-$C_3$alkynyl, phenyl, or phenyl$C_1$-$C_2$alkyl, wherein the phenyl moieties may be optionally substituted with 1, 2, or 3 groups, which may be the same or different, represented by $R^8$.

In one set of embodiments, $R^3$ is hydrogen, $C_1$-$C_4$alkyl, or N,N-di($C_1$-$C_3$alkyl)amino. Preferably, $R^3$ is hydrogen, $C_1$-$C_4$alkyl, or N,N-di(methyl)amino, more preferably, hydrogen or $C_1$-$C_3$alkyl. Even more preferably, $R^3$ is hydrogen, methyl or ethyl. More preferably still, $R^3$ is hydrogen or methyl.

$R^4$ is cyano, $C_2$-$C_6$alkenyl, $C_2$-$C_6$alkynyl, $C_1$-$C_6$alkoxy$C_2$-$C_6$alkenyl, $C_2$-$C_6$alkenyloxy$C_1$-$C_6$alkyl, $C_1$-$C_6$alkylcarbonyl, or hydroxycarbonyl.

Preferably, $R^4$ is cyano, $C_2$-$C_6$alkenyl, $C_2$-$C_6$alkynyl, $C_1$-$C_4$alkoxy$C_2$-$C_3$alkenyl, $C_2$-$C_4$alkenyloxy$C_1$-$C_3$alkyl, $C_1$-$C_6$alkylcarbonyl, or hydroxycarbonyl.

More preferably, $R^4$ is $C_2$-$C_6$alkenyl, $C_2$-$C_6$alkynyl, $C_1$-$C_6$alkylcarbonyl, or hydroxycarbonyl. More preferably still, $R^4$ is $C_2$-$C_4$alkenyl, $C_2$-$C_4$alkynyl, $C_1$-$C_4$alkylcarbonyl, or hydroxycarbonyl. Even more preferably, $R^4$ is $C_2$-$C_3$alkenyl, $C_2$-$C_3$alkynyl, $C_1$-$C_3$alkylcarbonyl, or hydroxycarbonyl. In one set of embodiments, $R^4$ is vinyl, ethynyl, acetyl, or hydroxycarbonyl.

$R^5$ is halogen, $C_1$-$C_4$alkyl, $C_1$-$C_4$alkoxy, $C_1$-$C_4$haloalkyl, or $C_1$-$C_4$alkoxy$C_1$-$C_4$alkyl. Preferably, $R^5$ is $C_1$-$C_4$alkyl, $C_1$-$C_3$alkoxy, or $C_1$-$C_3$alkoxy$C_1$-$C_2$alkyl. More preferably, $R^5$ is $C_1$-$C_4$alkyl. More preferably still, $R^5$ is $C_1$-$C_3$alkyl. In one set of embodiments, $R^5$ is methyl.

$R^6$ is hydrogen, $C_1$-$C_3$alkyl, or $C_1$-$C_3$alkoxy. Preferably, $R^6$ is hydrogen or $C_1$-$C_3$alkyl. More preferably, $R^6$ is hydrogen, methyl or ethyl. More preferably still, $R^6$ is methyl.

$R^7$ is halogen, $C_1$-$C_3$alkyl, or $C_1$-$C_3$alkoxy. Preferably, $R^7$ is halogen, methyl, ethyl, methoxy or ethoxy. Even more preferably, $R^7$ is halogen, methyl, or methoxy. More preferably still, $R^7$ is halogen. Even more preferably still, $R^7$ is chloro.

$R^8$ is halogen, cyano, $C_1$-$C_3$alkyl, or $C_1$-$C_3$alkoxy. Preferably, $R^8$ is halogen, cyano, methyl, ethyl, methoxy, or ethoxy. More preferably, $R^8$ is chloro, bromo, fluoro, methyl, or methoxy.

In a compound of formula (I) according to the present invention, preferably:

X is O;

$R^1$ is $C_1$-$C_4$alkyl;

$R^2$ is phenyl or heteroaryl, wherein the heteroaryl moiety is a 5- or 6-membered aromatic ring which comprises 1, 2, or 3 heteroatoms individually selected from N, O and S, and wherein each phenyl and heteroaryl moiety may be optionally substituted with 1, 2, or 3 groups, which may be the same or different, represented by $R^7$;

$R^3$ is hydrogen, $C_1$-$C_4$alkyl, or N,N-di($C_1$-$C_3$alkyl)amino;

$R^4$ is $C_2$-$C_6$alkenyl, $C_2$-$C_6$alkynyl, $C_1$-$C_6$alkylcarbonyl, or hydroxycarbonyl;

$R^5$ is $C_1$-$C_4$alkyl; and $R^7$ is halogen.

In another set of embodiments, X is O;

$R^1$ is $C_1$-$C_3$alkyl;

$R^2$ is phenyl optionally substituted with 1 or 2 groups, which may be the same or different, represented by $R^7$;

$R^3$ is hydrogen, $C_1$-$C_4$alkyl, or N,N-di($C_1$-$C_3$alkyl)amino;

$R^4$ is cyano, $C_2$-$C_6$alkenyl, $C_2$-$C_6$alkynyl, $C_1$-$C_4$alkoxy$C_2$-$C_3$alkenyl, $C_2$-$C_4$alkenyloxy$C_1$-$C_3$alkyl, $C_1$-$C_6$alkylcarbonyl, or hydroxycarbonyl;

$R^5$ is $C_1$-$C_3$alkyl; and $R^7$ is halogen.

Compounds of the invention can be made as shown in the following schemes, in which, unless otherwise stated, the definition of each variable is as defined above for a compound of Formula (I). General methods for the production of compounds of Formula (I) are described below. Unless otherwise stated in the text, $R^1$, $R^2$, $R^3$, $R^4$, $R^5$, and X are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallisation, distillation and filtration.

Scheme 1

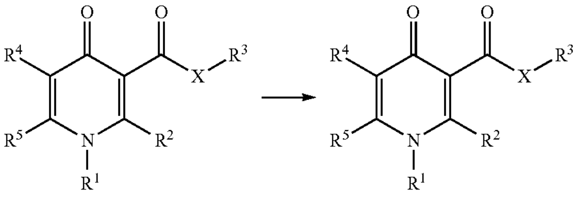

Formula (I) Formula (I)

Compounds of Formula (I) wherein X is NH and $R^3$ is —$N(CH_3)_2$ may be prepared by the coupling of a compound of Formula (I) wherein X is O and $R^3$ is hydrogen, with 1,1-dimethylhydrazine and a coupling agent such as propylphosphonic anhydride (used neat or as a solution in ethyl acetate) in a suitable solvent (such as dichloromethane or ethyl acetate) with an optional additive (such as dimethylaminopyridine). This is shown in Scheme 1 above. Compounds of Formula (I) may additionally be prepared by methods as described below.

Scheme 2

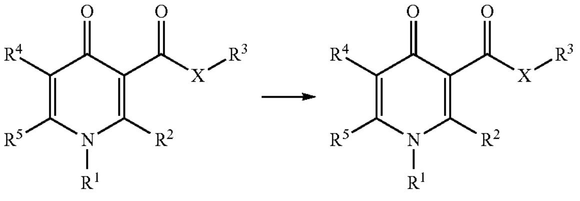

Formula (I) Formula (I)

Compounds of Formula (I) wherein X is O and $R^3$ is hydrogen, may be prepared by hydrolysis of a compound of Formula (I) wherein X is O and $R^3$ is not hydrogen, but any other $R^3$ group as defined above, with a suitable base (such as sodium hydroxide or lithium hydroxide) or with a suitable acid (such as trifluoroacetic acid, hydrochloric acid, formic acid or sulfuric acid) in a suitable solvent (such as methanol, ethanol, dichloromethane, chloroform, ethyl acetate or tetrahydrofuran) with an optional co-solvent (such as water). In the cases where a base was used, the product was obtained following acidification with a suitable acid (such as hydrochloric acid). In the cases where $R^4$ is pyridyl or pyridazinyl, the product was obtained as the equivalent salt (such as the hydrochloride salt). This is shown in Scheme 2 above. Compounds of Formula (I) may additionally be prepared by methods as described below.

Scheme 3

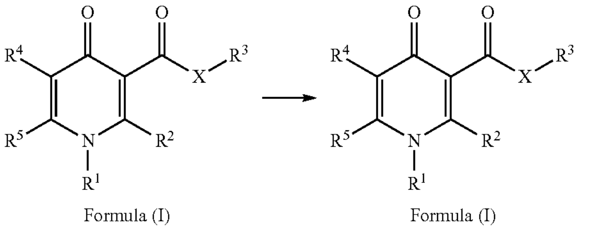

In an additional transformation, a compound of Formula (I) wherein $R^4$ is trimethylsilylethynyl may be converted to a compound of Formula (I) wherein $R^4$ is ethynyl by treatment with a base (such as potassium carbonate) in a solvent (such as methanol). This is shown in Scheme 3 above.

Scheme 4

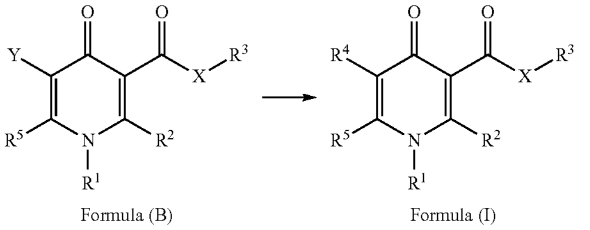

Compounds of Formula (I) wherein $R^4$ is an alkyne, alkene or ketone (such as trimethylsilylethynyl, vinyl or acetyl), may additionally be prepared from a compound of Formula (B) wherein Y is $C_1$, Br or I under Stille reaction conditions with, for instance, an alkynyl, alkenyl or ethyoxy vinyl stannane in the presence of a catalyst (such as tetrakis (triphenylphosphine)palladium(0) or dichlorobis(triphenylphosphine)palladium(II)) in a suitable solvent (such as toluene), at elevated temperature (for example 60° C., 120° C. or 125° C.). This is shown in Scheme 4 above.

Scheme 5

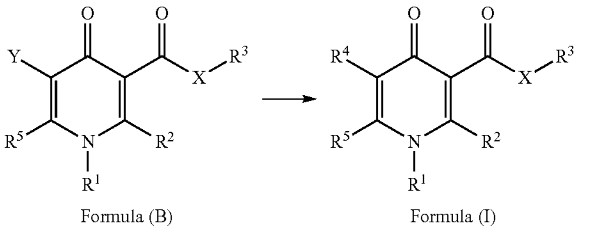

Compounds of Formula (I) wherein $R^4$ is a carboxylic acid may be prepared by treatment of a compound of Formula (B) wherein Y is Br with a Grignard reagent (such as isopropylmagnesium chloride lithium chloride complex) in a solvent (such as tetrahydrofuran) followed by reaction with gaseous carbon dioxide at temperatures between −20° C. and room temperature. This is shown in Scheme 5 above.

Scheme 6

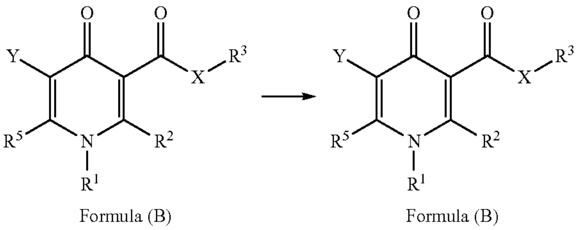

Compounds of Formula (B) wherein X is O, $R^3$ is hydrogen, and Y is Br or I, may be prepared by hydrolysis of a compound of Formula (B) wherein X is O and $R^3$ is not hydrogen, but any other $R^3$ group as defined above, with a suitable base (such as sodium hydroxide or lithium hydroxide) or with a suitable acid (such as trifluoroacetic acid, hydrochloric acid, formic acid or sulfuric acid) in a suitable solvent (such as methanol, ethanol, dichloromethane, chloroform, ethyl acetate or tetrahydrofuran) with an optional co-solvent (such as water). This is shown in Scheme 6 above.

Scheme 7

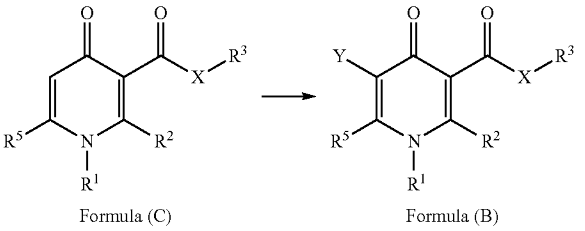

Compounds of Formula (B) wherein Y is Br or I may be prepared by treatment of compounds of Formula (C) with a suitable halogenating agent (such as N-iodo succinimide or N-bromo succinimide) in a suitable solvent (such as acetonitrile or trifluoroacetic acid). This is shown in Scheme 7 above.

Scheme 8

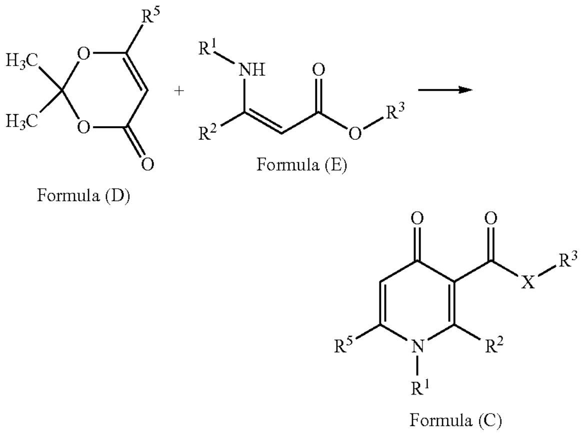

Compounds of Formula (C) wherein X is O, may be prepared by reacting a compound of Formula (D) with a compound of Formula (E) without a solvent and at an elevated temperature (for example 120° C.). Compounds of formula D are commercially available or may be prepared by methods familiar to persons skilled in the art. This is shown in Scheme 8 above.

Scheme 9

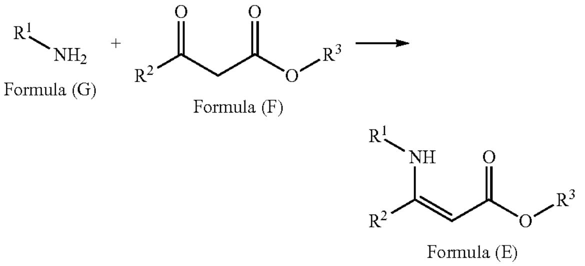

Formula (G) Formula (F) Formula (E)

Compounds of Formula (E) maybe be prepared from reaction of β-keto esters of Formula (F) with an amine salt. The amine salts can be prepared in situ by acidification of amines of Formula (G) with a suitable acid (such as acetic acid). These amine salts may then be reacted with compounds of Formula (F) in a suitable solvent (such as toluene) in the presence of an acid (such as acetic acid) and a drying agent (such as 4 Å molecular sieves. Compounds of Formula (F) are commercially available or may be prepared using conditions described below. Compounds of Formula (G) are commercially available or may be prepared by methods familiar to persons skilled in the art. This is shown in Scheme 9 above.

Scheme 10

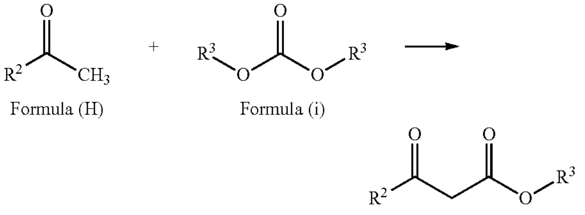

Formula (H) Formula (i) Formula (F)

Compounds of Formula (F) may be prepared by treatment of ketones of Formula (H) with a base (such as sodium hydride) in the presence of dialkyl carbonates of Formula (i) (such as dimethyl carbonate). Compounds of Formula (H) and Formula (i) are commercially available or may be prepared by methods familiar to persons skilled in the art. This is shown in Scheme 10 above.

The present invention still further provides a method of controlling weeds at a locus said method comprising application to the locus of a weed controlling amount of a composition comprising a compound of Formula (I). Moreover, the present invention may further provide a method of selectively controlling weeds at a locus comprising useful (crop) plants and weeds, wherein the method comprises application to the locus of a weed controlling amount of a composition according to the present invention. 'Controlling' means killing, reducing or retarding growth or preventing or reducing germination. It is noted that the compounds of the present invention show a much improved selectivity compared to know, structurally similar compounds. Generally the plants to be controlled are unwanted plants (weeds). 'Locus' means the area in which the plants are growing or will grow. The application may be applied to the locus pre-emergence and/or postemergence of the crop plant. Some crop plants may be inherently tolerant to herbicidal effects of compounds of Formula (I).

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2500 g/ha, especially from 25 to 1000 g/ha, more especially from 25 to 250 g/ha.

The application is generally made by spraying the composition, typically by tractor mounted sprayer for large areas, but other methods such as dusting (for powders), drip or drench can also be used.

The term "useful plants" is to be understood as also including useful plants that have been rendered tolerant to herbicides like bromoxynil or classes of herbicides such as, for example, 4-Hydroxyphenylpyruvate dioxygenase (HPPD) inhibitors, ALS inhibitors, for example primisulfuron, prosulfuron and trifloxysulfuron, 5-enol-pyrovyl-shikimate-3-phosphate-synthase (EPSPS) inhibitors, glutamine synthetase (GS) inhibitors or protoporphyrinogen-oxidase (PPO) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

The compounds of Formula (I) (or compositions comprising such) can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*.

Compounds of Formula (I) may be used in unmodified form or, preferably, together with the adjuvants conventionally employed in the art of formulation to provide herbicidal compositions, using formulation adjuvants, such as carriers, solvents and surface-active agents (SAA). The invention therefore further provides a herbicidal composition, comprising at least one compound Formula (I) and an agriculturally acceptable carrier and optionally an adjuvant. An agricultural acceptable carrier is for example a carrier that is suitable for agricultural use. Agricultural carriers are well known in the art.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types. These include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a soluble powder (SP), a wettable powder (WP) and a soluble granule (SG). The formulation type chosen in any instance will depend upon the particular purpose envisaged and the physical, chemical and biological properties of the compound of Formula (I).

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SAAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SAAs, to produce spontaneously a thermodynamically stable isotropic liquid formulation. A compound of Formula (I) is present initially in either the water or the solvent/SAA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SAAs), spray additives based on oils, for example certain mineral oils or natural plant oils (such as soy bean and rape seed oil), modified plant oils such as methylated rape seed oil (MRSO), and blends of these with other bio-enhancing adjuvants (ingredients which may aid or modify the action of a compound of Formula (I).

Wetting agents, dispersing agents and emulsifying agents may be SAAs of the cationic, anionic, amphoteric or non-ionic type.

Suitable SAAs of the cationic type include quaternary ammonium compounds (for example cetyltrimethyl ammonium bromide), imidazolines and amine salts.

Suitable anionic SAAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates, lignosulphonates and phosphates/sulphates of tristyrylphenols.

Suitable SAAs of the amphoteric type include betaines, propionates and glycinates.

Suitable SAAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); lecithins and sorbitans and esters thereof, alkyl polyglycosides and tristyrylphenols.

Suitable suspending agents include hydrophilic colloids (such as polysaccharides, polyvinylpyrrolidone or sodium carboxymethylcellulose) and swelling clays (such as bentonite or attapugite).

The compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, beflubutamid-M, benquitrione, bensulfuron (including bensulfuron-methyl), bentazone, bicyclopyrone, bilanafos, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chlorotoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, diquat dibromide, diuron, epyrifenacil, ethalfluralin, ethofumesate, fenoxaprop (including fenoxaprop-P-ethyl), fenoxasulfone, fenquinotrione, fentrazamide, flazasulfuron, florasulam, florpyrauxifen (including florpyrauxifen-benzyl), fluazifop (including fluazifop-P-butyl), flucarbazone (including flucarbazone-sodium), flufenacet, flumetsulam, flumioxazin, fluometuron, flupyrsulfuron (including flupyrsulfuron-methyl-sodium), fluroxypyr (including fluroxypyr-meptyl), fomesafen, foramsulfuron, glufosinate (including L-glufosinate and the ammonium salts of both), glyphosate (including the diammonium, isopropylammonium and potassium salts thereof), halauxifen (including halauxifen-methyl), haloxyfop (including haloxyfop-methyl), hexazinone, hydantocidin, imazamox (including R-imazamox), imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, prometryne, propanil, propaquizafop, propyrisulfuron, propyzamide, prosulfocarb, prosulfuron, pyraclonil, pyraflufen (including pyraflufen-ethyl), pyrasulfotole, pyridate, pyriftalid, pyrimisulfan, pyroxasulfone, pyroxsulam, quinclorac, quinmerac, quizalofop (including quizalofop-P-ethyl and quizalofop-P-tefuryl), rimsulfuron, saflufenacil, sethoxydim, simazine, S-metalochlor, sulfentrazone, sulfosulfuron, tebuthiuron, tefuryltrione, tembotrione, terbuthylazine, terbutryn, tetflupyrolimet, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, 3-(2-chloro-4-fluoro-5-(3-methyl-2,6-dioxo-4-trifluoromethyl-3,6-dihydropyrimidin-1(2H)-yl) phenyl)-5-methyl-4,5-dihydroisoxazole-5-carboxylic acid ethyl ester, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl] imidazolidin-2-one, (4R)1-(5-tert-butylisoxazol-3-yl)-4-ethoxy-5-hydroxy-3-methyl-imidazolidin-2-one, 3-[2-(3,4-dimethoxyphenyl)-6-methyl-3-oxo-pyridazine-4-carbonyl] bicyclo[3.2.1]octane-2,4-dione, 2-[2-(3,4-dimethoxyphenyl)-6-methyl-3-oxo-pyridazine-4-carbonyl]-5-methyl-cyclohexane-1,3-dione, 2-[2-(3,4-dimethoxyphenyl)-6-methyl-3-oxo-pyridazine-4-carbonyl] cyclohexane-1,3-dione, 2-[2-(3,4-dimethoxyphenyl)-6-methyl-3-oxo-pyridazine-4-carbonyl]-5,5-dimethyl-cyclohexane-1,3-dione, 6-[2-(3,4-dimethoxyphenyl)-6-methyl-3-oxo-pyridazine-4-carbonyl]-2,2,4,4-tetramethyl-cyclohexane-1,3,5-trione, 2-[2-(3,4-dimethoxyphenyl)-6-methyl-3-oxo-pyridazine-4-carbonyl]-5-ethyl-cyclohexane-1,3-dione, 2-[2-(3,4-dimethoxyphenyl)-6-methyl-3-oxo-pyridazine-4-carbonyl]-4,4,6,6-tetramethyl-cyclohexane-1,3-dione, 2-[6-cyclopropyl-2-(3,4-dimethoxyphenyl)-3-oxo-pyridazine-4-carbonyl]-5-methyl-cyclohexane-1,3-dione, 3-[6-cyclopropyl-2-(3,4-dimethoxyphenyl)-3-oxo-pyridazine-4-carbonyl]bicyclo[3.2.1]octane-2,4-dione, 2-[6-cyclopropyl-2-(3,4-dimethoxyphenyl)-3-oxo-pyridazine-4-carbonyl]-5,5-dimethyl-cyclohexane-1,3-dione, 6-[6-cyclopropyl-2-(3,4-dimethoxyphenyl)-3-oxo-pyridazine-4-carbonyl]-2,2,4,4-tetramethyl-cyclohexane-1,3,5-trione, 2-[6-cyclopropyl-2-(3,4-dimethoxyphenyl)-3-oxo-pyridazine-4-carbonyl]cyclohexane-1,3-dione, 4-[2-(3,4-dimethoxyphenyl)-6-methyl-3-oxo-pyridazine-4-carbonyl]-2,2,6,6-tetramethyl-tetrahydropyran-3,5-dione, 4-[6-cyclopropyl-2-(3,4-dimethoxyphenyl)-3-oxo-pyridazine-4-carbonyl]-2,2,6,6-tetramethyl-tetrahydropyran-3,5-dione, 4-amino-3-chloro-5-fluoro-6-(7-fluoro-1H-indol-6-yl)pyridine-2-carboxylic acid (including agrochemically acceptable esters thereof, for example, methyl 4-amino-3-chloro-5-fluoro-6-(7-fluoro-1H-indol-6-yl)pyridine-2-carboxylate, prop-2-ynyl 4-amino-3-chloro-5-fluoro-6-(7-fluoro-1H-indol-6-yl)pyridine-2-carboxylate and cyanomethyl 4-amino-3-chloro-5-fluoro-6-(7-fluoro-1H-indol-6-yl)pyridine-2-carboxylate), 3-ethylsulfanyl-N-(1,3,4-oxadiazol-2-yl)-5-(trifluoromethyl)-[1,2,4]triazolo[4,3-a]pyridine-8-carboxamide, 3-(isopropylsulfanylmethyl)-N-(5-methyl-1,3,4-oxadiazol-2-yl)-5-(trifluoromethyl)-[1,2,4]triazolo[4,3-a]pyridine-8-carboxamide, 3-(isopropylsulfonylmethyl)-N-(5-methyl-1,3,4-oxadiazol-2-yl)-5-(trifluoromethyl)-[1,2,4]triazolo[4,3-a]pyridine-8-carboxamide, 3-(ethylsulfonylmethyl)-N-(5-methyl-1,3,4-oxadiazol-2-yl)-5-(trifluoromethyl)-[1,2,4]triazolo[4,3-a]pyridine-8-carboxamide, ethyl 2-[[3-[[3-chloro-5-fluoro-6-[3-methyl-2,6-dioxo-4-(trifluoromethyl)pyrimidin-1-yl]-2-pyridyl]oxy]acetate, 6-chloro-4-(2,7-dimethyl-1-naphthyl)-5-hydroxy-2-methyl-pyridazin-3-one, 1-[2-chloro-6-(5-chloropyrimidin-2-yl)oxy-phenyl]-4,4,4-trifluoro-butan-1-one and 5-[2-chloro-6-(5-chloropyrimidin-2-yl)oxy-phenyl]-3-(difluoromethyl)isoxazole.

The mixing partners of the compound of Formula (I) may also be in the form of esters or salts, as mentioned e.g. in The Pesticide Manual, Sixteenth Edition, British Crop Protection Council, 2012. The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil. Particularly preferred are mixtures of a compound of Formula (I) with cyprosulfamide, isoxadifen-ethyl, cloquintocet-mexyl and/or metcamifen.

The safeners of the compound of Formula (I) may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048.

Preferably the mixing ratio of compound of Formula (I) to safener is from 100:1 to 1:10, especially from 20:1 to 1:1.

The compounds of Formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of Formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compound of Formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The tables below illustrate examples of individual compounds of Formula (I) according to the invention:

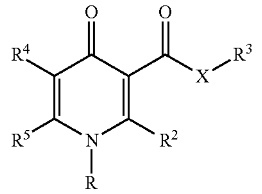

(I)

TABLE 1

Individual compounds of formula (I) according to the invention

| Cpd No. | $R^4$ | $R^5$ |
|---|---|---|
| 001 | vinyl | methyl |
| 002 | vinyl | ethyl |
| 003 | vinyl | methoxymethyl |
| 004 | ethynyl | methyl |
| 005 | ethynyl | ethyl |
| 006 | ethynyl | methoxymethyl |
| 007 | acetyl | methyl |
| 008 | acetyl | ethyl |
| 009 | acetyl | methoxymethyl |
| 010 | carboxy | methyl |
| 011 | carboxy | ethyl |
| 012 | carboxy | methoxymethyl |

Table A-1 provides 12 compounds A-1.001 to A.1.012 of Formula (I) wherein X is O, $R^1$ is methyl, $R^2$ is 3,4-dichlorophenyl, $R^3$ is hydrogen, and $R^4$ and $R^5$ are as defined in Table 1.

Table A-2 provides 12 compounds A-2.001 to A.2.012 of Formula (I) wherein X is O, $R^1$ is ethyl, $R^2$ is 3,4-dichlorophenyl, $R^3$ is hydrogen, and $R^4$ and $R^5$ are as defined in Table 1.

Table A-3 provides 12 compounds A-3.001 to A.3.012 of Formula (I) wherein X is O, $R^1$ is methyl, $R^2$ is 3,4-dichlorophenyl, $R^3$ is methyl, and $R^4$ and $R^5$ are as defined in Table 1.

Table A-4 provides 12 compounds A-4.001 to A.4.012 of Formula (I) wherein X is O, $R^1$ is ethyl, $R^2$ is 3,4-dichlorophenyl, $R^3$ is methyl, and $R^4$ and $R^5$ are as defined in Table 1.

Table A-5 provides 12 compounds A-5.001 to A.5.012 of Formula (I) wherein X is NH, $R^1$ is methyl, $R^2$ is 3,4-dichlorophenyl, $R^3$ is —$N(CH_3)_2$, and $R^4$ and $R^5$ are as defined in Table 1.

Table A-6 provides 12 compounds A-6.001 to A.6.012 of Formula (I) wherein X is NH, $R^1$ is ethyl, $R^2$ is 3,4-dichlorophenyl, $R^3$ is —$N(CH_3)_2$, and $R^4$ and $R^5$ are as defined in Table 1.

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients.

The medium capsule diameter is 8-15 microns. The resulting formulation is applied to seeds as an aqueous suspension in an apparatus suitable for that purpose.

EXAMPLES

The following non-limiting examples provide specific synthesis methods for representative compounds of the present invention, as referred to in Table 2 below.

List of Abbreviations

Å=angstrom, ° C.=degrees Celsius, d=doublet, DMSO=dimethyl sulfoxide, HPLC=high performance liquid chromatography, LCMS=liquid chromatography mass spectrometry, M=molar, m=multiplet, MHz=megahertz, q=quartet, s=singlet, t=triplet, THF=tetrahydrofuran, TMT=2,4,6-trimethylmercaptotriazine.

Example 1: Synthesis of methyl 2-(3,4-dichlorophenyl)-1-ethyl-6-methyl-4-oxo-5-vinyl-pyridine-3-carboxylate (Compound 4.001)

Step 1: Synthesis of methyl 3-(3,4-dichlorophenyl)-3-oxo-propanoate

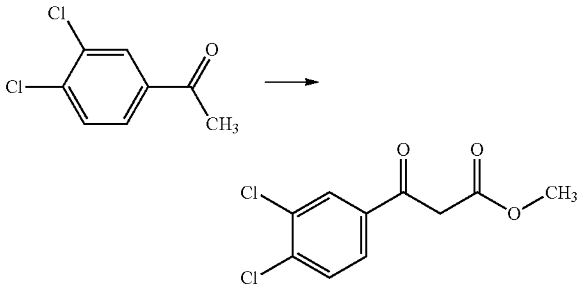

To a stirred solution of 1-(3,4-dichlorophenyl)ethanone (5.00 g, 26.5 mmol) and dimethyl carbonate (40 mL, 466 mmol) under nitrogen, cooled to 0° C. was added portion-wise sodium hydride (3.17 g, 79.5 mmol, 60 mass %). The reaction mixture was allowed to warm to room temperature and stirred for 16 hours. Overnight the reaction mixture became a solid paste which was not possible to stir. More dimethyl carbonate (10 mL) was added in an attempt to create a mobile slurry for quenching. The reaction mixture was cooled to 0° C. and quenched by addition of water (25 mL) under nitrogen. The reaction mixture was acidified to pH 3 by addition of 2M aqueous hydrochloric acid and then extracted with ethyl acetate. The organic extract was dried over magnesium sulfate and evaporated to dryness under reduced pressure. The crude residue was purified by flash chromatography on silica gel using a gradient of 0-15% ethyl acetate in isohexane as eluent to give methyl 3-(3,4-dichlorophenyl)-3-oxo-propanoate (mixture of tautomers) as a colourless liquid (5.78 g, 23.5 mmol, 89%).

Enol: $^1$H NMR (400 MHz, chloroform) δ=12.47 (s, 1H), 7.87 (d, 1H), 7.59 (m, 3H), 7.49 (d, 1H), 5.65 (s, 1H), 3.82 (s, 3H)

Keto: $^1$H NMR (400 MHz, chloroform) δ=8.03 (d, 1H), 7.77 (m, 1H), 7.58 (d, 2H), 3.97 (s, 2H), 3.76 (s, 3H).

Step 2: Synthesis of methyl (Z)-3-(3,4-dichlorophenyl)-3-(ethylamino)prop-2-enoate

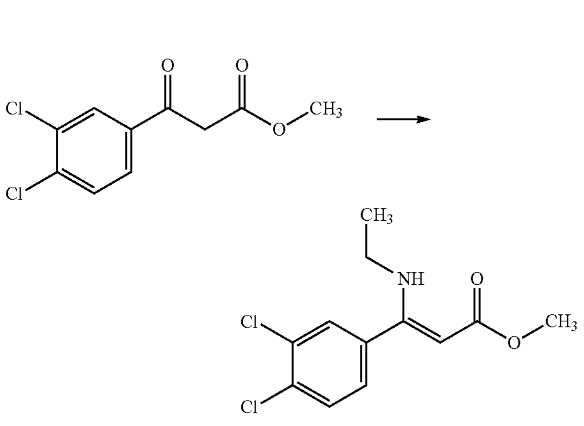

To a stirred solution of ethylamine (2M in THF) (12.2 mL, 24.34 mmol) at 0° C. was added dropwise acetic acid (1.39 mL, 24.3 mmol). The mixture was allowed to warm to room temperature and stirred for 1 hour before being evaporated to dryness under reduced pressure to afford ethylammonium acetate (2.55 g, 24.3 mmol). The ethylammonium acetate (2.55 g, 24.3 mmol) was added to a solution of methyl 3-(3,4-dichlorophenyl)-3-oxo-propanoate (2.00 g, 8.09 mmol) in toluene (20 mL) followed by addition of acetic acid (0.46 mL, 8.09 mmol) and powdered 4 Å molecular sieves. The reaction mixture was heated at reflux for 18 hours. The cooled reaction mixture was diluted with ethyl acetate, filtered and washed with saturated aqueous sodium bicarbonate solution. The phases were separated and the aqueous was extracted with ethyl acetate (×3). The combined organic extracts were washed with brine, dried over magnesium sulfate and evaporated to dryness under reduced pressure. The crude residue was purified by flash chromatography on silica gel using a gradient of 0-10% ethyl acetate in isohexane as eluent to give methyl (Z)-3-(3,4-dichlorophenyl)-3-(ethylamino)prop-2-enoate as a pale yellow oil (1.54 g, 5.61 mmol, 69%).

$^1$H NMR (400 MHz, chloroform) δ=8.37 (br s, 1H), 7.48 (d, 1H), 7.46 (d, 1H), 7.20 (m, 1H), 4.55 (s, 1H), 3.68 (s, 3H), 3.07 (m, 2H), 1.13-1.09 (m, 3H).

Step 3: Synthesis of methyl 2-(3,4-dichlorophenyl)-1-ethyl-6-methyl-4-oxo-pyridine-3-carboxylate

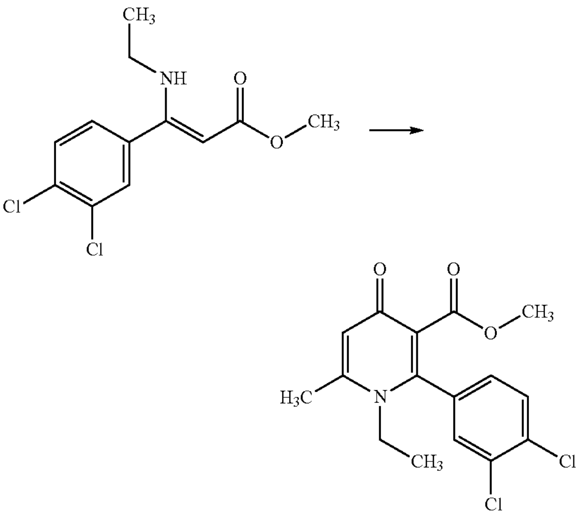

A stirred mixture of methyl (Z)-3-(3,4-dichlorophenyl)-3-(ethylamino)prop-2-enoate (1.50 g, 5.5 mmol) and 2,2,6-trimethyl-1,3-dioxin-4-one (0.82 g, 5.5 mmol) under nitrogen were heated at 120° C. for 3 hours. The cooled reaction mixture was evaporated to dryness under reduced pressure. The crude residue was purified by flash chromatography on silica gel using a gradient of 0-10% methanol in dichloromethane as eluent to give methyl 2-(3,4-dichlorophenyl)-1-ethyl-6-methyl-4-oxo-pyridine-3-carboxylate as an off-white solid (0.95 g, 2.78 mmol, 51%).

$^1$H NMR (400 MHz, chloroform) δ=7.56 (d, 1H), 7.50 (d, 1H), 7.24 (m, 1H), 6.41 (s, 1H), 3.72 (q, 2H), 3.55 (s, 3H), 2.42 (s, 3H), 1.13 (t, 3H).

Step 4: Synthesis of methyl 2-(3,4-dichlorophenyl)-1-ethyl-5-iodo-6-methyl-4-oxo-pyridine-3-carboxylate

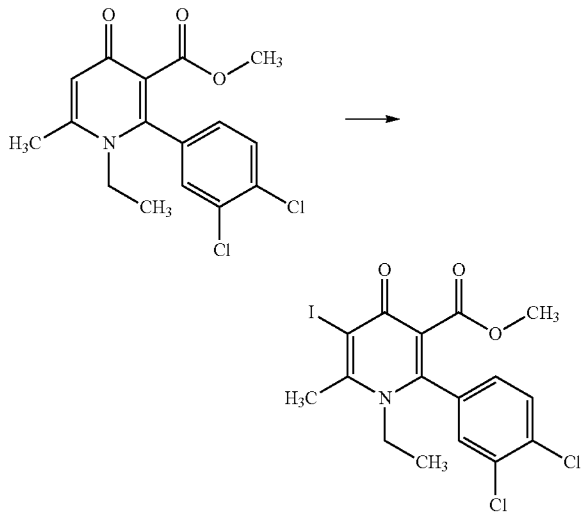

To a solution of methyl 2-(3,4-dichlorophenyl)-1-ethyl-6-methyl-4-oxo-pyridine-3-carboxylate (5.60 g, 16.5 mmol) in acetonitrile (56.0 mL) at room temperature and under nitrogen was added 1-iodopyrrolidine-2,5-dione (3.70 g, 16.5 mmol) followed by 2,2,2-trifluoroacetic acid (0.564 g, 0.381 mL, 4.94 mmol). The reaction mixture was heated at 80° C. for 36 hours and then stirred at room temperature for 48 hours. The cooled reaction mixture was quenched by addition of saturated aqueous sodium hydrogen carbonate solution (200 mL) and extracted with dichloromethane (×3). The combined organic extracts were washed with saturated sodium thiosulfate solution then brine, dried over magnesium sulfate, filtered and evaporated under reduced pressure. The crude residue was purified by flash chromatography on silica gel using a gradient of 0-100% ethyl acetate in cyclohexane as eluent to give methyl 2-(3,4-dichlorophenyl)-1-ethyl-5-iodo-6-methyl-4-oxo-pyridine-3-carboxylate as a white solid (5.33 g, 11.4 mmol, 70%).

$^1$H NMR (400 MHz, chloroform) δ=7.57 (d, 1H), 7.49 (d, 1H), 7.23 (m, 1H), 3.89 (q, 2H), 3.57 (s, 3H), 2.88 (s, 3H), 1.17 (t, 3H).

Step 5: Synthesis of methyl 2-(3,4-dichlorophenyl)-1-ethyl-6-methyl-4-oxo-5-vinyl-pyridine-3-carboxylate

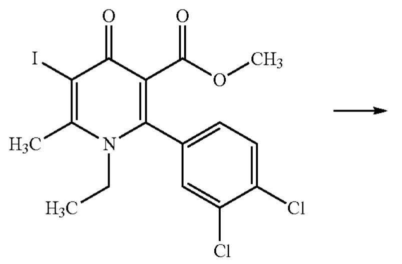

-continued

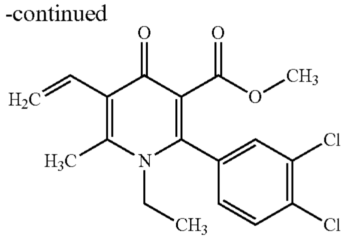

To a mixture of methyl 2-(3,4-dichlorophenyl)-1-ethyl-5-iodo-6-methyl-4-oxo-pyridine-3-carboxylate (0.270 g, 0.58 mmol) and dichlorobis(triphenylphosphine)palladium(II) (0.021 g, 0.029 mmol) under nitrogen was added degassed toluene (4 mL) followed by tributyl(vinyl)stannane (0.551 g, 1.74 mmol). The mixture was heated under microwave irradiation at 140° C. for 0.75 hours. The reaction mixture was evaporated to dryness under reduced pressure and purified by flash chromatography on silica gel using a gradient of 0-100% ethyl acetate in cyclohexane as eluent to give methyl 2-(3,4-dichlorophenyl)-1-ethyl-6-methyl-4-oxo-5-vinyl-pyridine-3-carboxylate (0.155 g, 0.423 mmol, 73%).

$^1$H NMR (400 MHz, chloroform) δ=7.55 (d, 1H), 7.50 (d, 1H), 7.24 (m, 1H), 6.63 (m, 1H), 5.99 (m, 1H), 5.62 (m, 1H), 3.80 (q, 2H), 3.57 (s, 3H), 2.54 (s, 3H), 1.15 (t, 3H).

Example 2: Synthesis of 2-(3,4-dichlorophenyl)-1-ethyl-5-ethynyl-6-methyl-4-oxo-pyridine-3-carboxylic acid (Compound 2.005)

Step 1: Synthesis of 2-(3,4-dichlorophenyl)-1-ethyl-5-iodo-6-methyl-4-oxo-pyridine-3-carboxylic acid

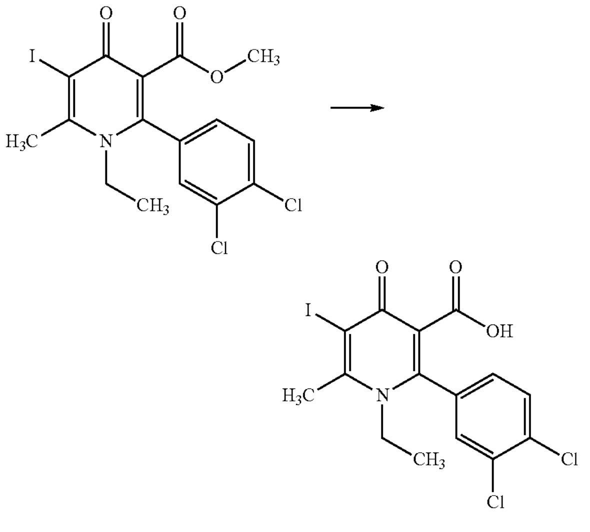

To a solution of methyl 2-(3,4-dichlorophenyl)-1-ethyl-5-iodo-6-methyl-4-oxo-pyridine-3-carboxylate (0.329 g, 0.706 mmol) in methanol (4 mL) and water (2 mL) was added lithium hydroxide monohydrate (0.059 g, 1.41 mmol). The reaction mixture was heated to 80° C. for 6 hours. The reaction mixture was evaporated under reduced pressure. The residue was diluted with water (15 mL) and extracted with dichloromethane. The aqueous phase was acidified to pH 3 by addition of 2M aqueous hydrochloric acid before further extraction with dichloromethane (2×10 mL). The organic extracts were dried and then evaporated to dryness under reduced pressure to give 2-(3,4-dichlorophenyl)-1-ethyl-5-iodo-6-methyl-4-oxo-pyridine-3-carboxylic acid (0.311 g, 0.69 mmol, 98%) as a white solid.

$^1$H NMR (400 MHz, chloroform) δ=7.60 (d, 1H), 7.34 (d, 1H), 7.10 (m, 1H), 4.01 (q, 2H), 2.99 (s, 3H), 1.23 (t, 3H).

Step 2: Synthesis of 2-(3,4-dichlorophenyl)-1-ethyl-6-methyl-4-oxo-5-(2-trimethylsilylethynyl)pyridine-3-carboxylic acid

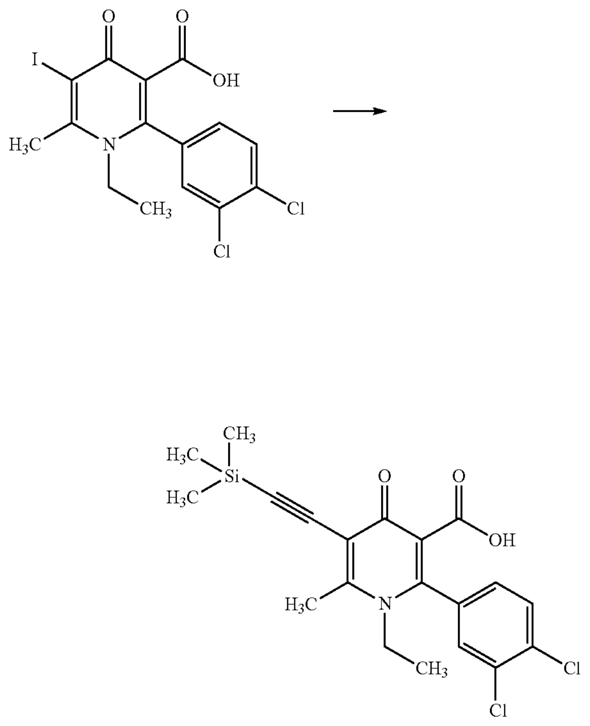

To a mixture of 2-(3,4-dichlorophenyl)-1-ethyl-5-iodo-6-methyl-4-oxo-pyridine-3-carboxylic acid (0.150 g, 0.332 mmol) and tetrakis(triphenylphosphine)palladium(0) (0.077 g, 0.066 mmol) at room temperature and under nitrogen was added degassed toluene (1 mL). Tributyl(trimethylsilylethynyl)tin (0.308 g, 0.796 mmol) was added and the reaction mixture was heated under microwave irradiation at 120° C. for 0.5 hours. The cooled reaction mixture was passed through a TMT column and the filtrate was evaporated to dryness under reduced pressure. The crude residue was purified by mass-directed reverse phase HPLC to give 2-(3,4-dichlorophenyl)-1-ethyl-6-methyl-4-oxo-5-(2-trimethylsilylethynyl)pyridine-3-carboxylic acid (0.022 g, 0.052 mmol, 16%) as a yellow solid.

$^1$H NMR (400 MHz, chloroform) δ=7.59 (d, 1H), 7.33 (d, 1H), 7.09 (m, 1H), 3.89 (q, 2H), 2.81 (s, 3H), 1.21 (t, 3H), 0.31 (s, 9H).

Step 3: Synthesis of 2-(3,4-dichlorophenyl)-1-ethyl-5-ethynyl-6-methyl-4-oxo-pyridine-3-carboxylic acid

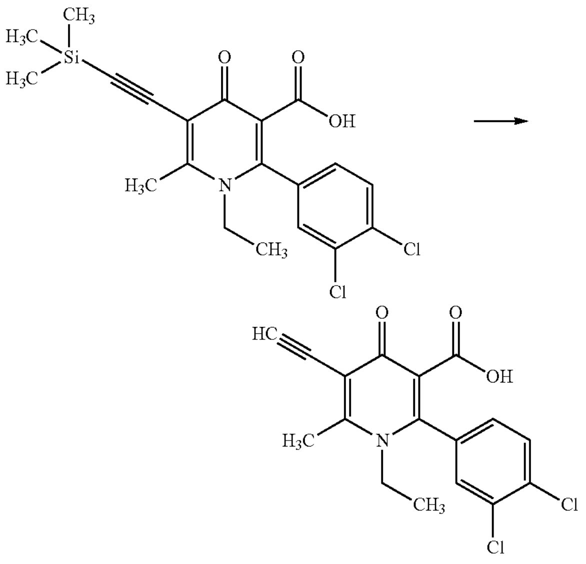

To a solution of 2-(3,4-dichlorophenyl)-1-ethyl-6-methyl-4-oxo-5-(2-trimethylsilylethynyl)pyridine-3-carboxylic acid (0.022 g, 0.052 mmol) in methanol (0.52 mL) at room temperature was added potassium carbonate (0.016 g, 0.115 mmol). The reaction mixture was stirred at room temperature for 18 hours. The reaction mixture was diluted with ethyl acetate (20 mL) and aqueous hydrochloric acid (2M, 20 mL). The aqueous phase was extracted with ethyl acetate (×2). The combined organic extracts were washed with water, dried over magnesium sulfate and evaporated to dryness under reduced pressure. The crude residue was purified by mass-directed HPLC to give 2-(3,4-dichlorophenyl)-1-ethyl-5-ethynyl-6-methyl-4-oxo-pyridine-3-carboxylic acid (0.017 g, 0.048 mmol, 92%) as a white solid.

$^1$H NMR (400 MHz, acetonitrile-$d_3$) δ=7.69 (d, 1H), 7.51 (d, 1H), 7.27 (m, 1H), 3.99 (s, 1H), 3.89 (q, 2H), 2.80 (s, 3H), 1.12 (t, 3H).

Example 3: Synthesis of 2-(3,4-dichlorophenyl)-1-ethyl-6-methyl-4-oxo-5-vinyl-pyridine-3-carboxylic acid (Compound 2.001)

Step 1: Synthesis of methyl 5-bromo-2-(3,4-dichlorophenyl)-1-ethyl-6-methyl-4-oxo-pyridine-3-carboxylate

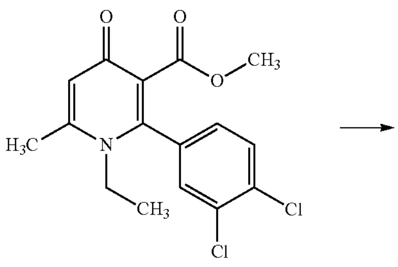

-continued

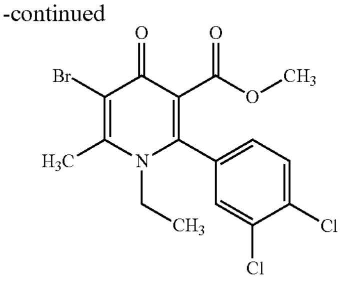

To a stirred solution of methyl 2-(3,4-dichlorophenyl)-1-ethyl-6-methyl-4-oxo-pyridine-3-carboxylate (0.500 g, 1.47 mmol) in acetonitrile (5.0 mL, 95.7 mmol) at room temperature was added portion-wise N-bromosuccinimide (0.26 g, 1.47 mmol). The reaction mixture was stirred at room temperature until LCMS indicated full consumption of starting material. The reaction mixture was quenched by addition of saturated aqueous sodium hydrogen carbonate solution (30 mL) and the aqueous phase was extracted with dichloromethane (3x15 mL). The combined organic extracts were passed through a phase separator and evaporated to dryness under reduced pressure. The crude residue was purified by flash chromatography on silica gel using a gradient of 50-100% ethyl acetate in isohexane as eluent to give methyl 5-bromo-2-(3,4-dichlorophenyl)-1-ethyl-6-methyl-4-oxo-pyridine-3-carboxylate as a colourless solid (0.602 g, 1.44 mmol, 98%).

$^1$H NMR (400 MHz, chloroform) δ=7.57 (d, 1H), 7.49 (d, 1H), 7.23 (m, 1H), 3.85 (q, 2H), 3.57 (s, 3H), 2.74 (s, 3H), 1.17 (t, 3H).

Step 2: Synthesis of 5-bromo-2-(3,4-dichlorophenyl)-1-ethyl-6-methyl-4-oxo-pyridine-3-carboxylic acid

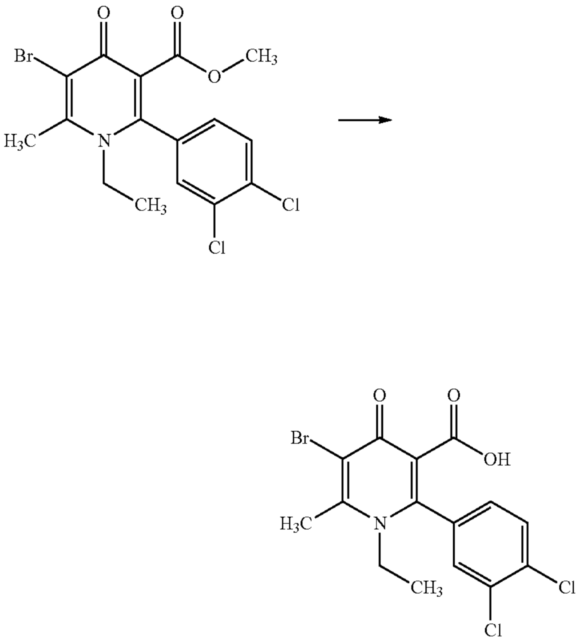 [SMILES: CCn1c(C)cc(=O)c(C(=O)OC)c1-c1ccc(Cl)c(Cl)c1 ; CCn1c(C)c(I)c(=O)c(C(=O)OC)c1-c1ccc(Cl)c(Cl)c1]

To a solution of methyl 5-bromo-2-(3,4-dichlorophenyl)-1-ethyl-6-methyl-4-oxo-pyridine-3-carboxylate (2.50 g, 5.97 mmol) in methanol (15 mL) was added a solution of lithium hydroxide monohydrate (1.00 g, 23.9 mmol) in water (6 mL). The resultant solution was heated to 80° C. for 2 hours. The cooled reaction mixture was acidified to pH 1-2 by addition of concentrated hydrochloric acid. The precipitated solid was collected by filtration, washed with cold water and dried to give 5-bromo-2-(3,4-dichlorophenyl)-1-ethyl-6-methyl-4-oxo-pyridine-3-carboxylic acid as a white powder (1.84 g, 4.54 mmol, 76%).

$^1$H NMR (400 MHz, methanol-$d_4$) δ=7.68 (d, 1H), 7.64 (d, 1H), 7.33 (m, 1H), 4.03 (q, 2H), 2.89 (s, 3H), 1.19 (t, 3H).

Step 3: Synthesis of 2-(3,4-dichlorophenyl)-1-ethyl-6-methyl-4-oxo-5-vinyl-pyridine-3-carboxylic acid

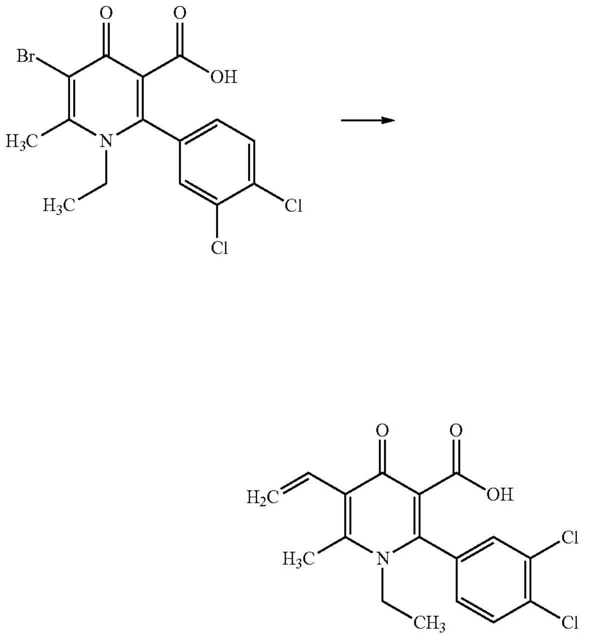

To dichlorobis(triphenylphosphine)palladium(II) under nitrogen was added a solution of 5-bromo-2-(3,4-dichlorophenyl)-1-ethyl-6-methyl-4-oxo-pyridine-3-carboxylic acid (0.300 g, 0.741 mmol) in toluene (5 mL). The mixture was degassed under nitrogen for 5 minutes after which time tributyl(vinyl)stannane (0.704 g, 2.22 mmol) was added. The reaction mixture was heated under microwave irradiation at 120° C. for 0.75 hours. The cooled reaction mixture was filtered through diatomaceous earth and evaporated to dryness under reduced pressure. The crude residue was purified by flash chromatography on silica gel using a gradient of 5-100% ethyl acetate in cyclohexane as eluent to give 2-(3,4-dichlorophenyl)-1-ethyl-6-methyl-4-oxo-5-vinyl-pyridine-3-carboxylic acid (0.099 g, 0.28 mmol, 38%).

$^1$H NMR (400 MHz, chloroform) δ=7.63-7.56 (m, 1H), 7.39-7.33 (m, 1H), 7.15-7.07 (m, 1H), 6.73-6.58 (m, 1H), 5.83-5.80 (m, 1H), 5.79-5.71 (m, 1H), 3.95-3.87 (m, 2H), 2.68-2.61 (m, 3H), 1.26-1.15 (m, 3H).

Example 4: Synthesis of 5-acetyl-2-(3,4-dichlorophenyl)-1-ethyl-6-methyl-4-oxo-pyridine-3-carboxylic acid (Compound 2.008)

Step 1: Synthesis of methyl 5-acetyl-2-(3,4-dichlorophenyl)-1-ethyl-6-methyl-4-oxo-pyridine-3-carboxylate

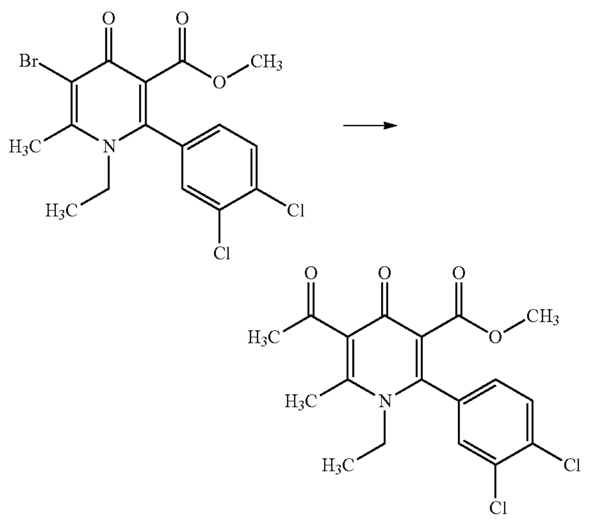

A solution of methyl 5-bromo-2-(3,4-dichlorophenyl)-1-ethyl-6-methyl-4-oxo-pyridine-3-carboxylate (0.462 g, 1.10 mmol) in toluene (15 mL) was added to dichlorobis(triphenylphosphine)palladium(II) (0.039 g, 0.055 mmol). Tributyl(1-ethoxyvinyl)stannane (1.194 g, 3.31 mmol) was added and the reaction mixture was heated to 60° C. for 1.5 hours and then at 125° C. for 5 hours. More dichlorobis(triphenylphosphine)palladium(II) (0.039 g, 0.055 mmol) and tributyl(1-ethoxyvinyl)stannane (1.194 g, 3.31 mmol) were added and the reaction mixture was heated for 18 hours. The cooled reaction mixture was evaporated to dryness under reduced pressure. The crude residue was purified by flash chromatography on silica gel using a gradient of 5-100% ethyl acetate in isohexane as eluent to give methyl 5-acetyl-2-(3,4-dichlorophenyl)-1-ethyl-6-methyl-4-oxo-pyridine-3-carboxylate (0.062 g, 0.16 mmol, 15%).

$^1$H NMR (400 MHz, chloroform) δ=7.65-7.64 (m, 1H), 7.58-7.56 (m, 1H), 7.31-7.30 (m, 1H), 4.18-4.06 (m, 2H), 3.60-3.49 (m, 3H), 2.63-2.53 (m, 3H), 2.43-2.37 (m, 3H), 1.29-1.22 (m, 3H).

Step 2: Synthesis of 5-acetyl-2-(3,4-dichlorophenyl)-1-ethyl-6-methyl-4-oxo-pyridine-3-carboxylic acid

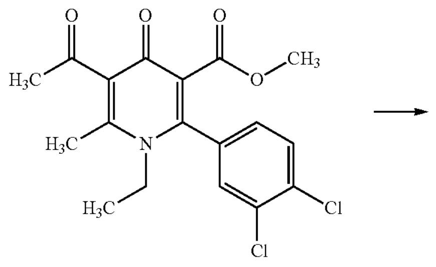

-continued

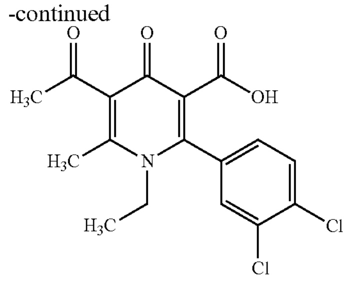

Prepared as for 5-bromo-2-(3,4-dichlorophenyl)-1-ethyl-6-methyl-4-oxo-pyridine-3-carboxylic acid using methyl 5-acetyl-2-(3,4-dichlorophenyl)-1-ethyl-6-methyl-4-oxo-pyridine-3-carboxylate (0.062 g, 0.16 mmol) and lithium hydroxide hydrate (0.027 g, 0.65 mmol) with stirring at room temperature for 1.5 hours followed by heating at reflux for 2 hours to give 5-acetyl-2-(3,4-dichlorophenyl)-1-ethyl-6-methyl-4-oxo-pyridine-3-carboxylic acid (0.034 g, 0.091 mmol, 56%).

$^1$H NMR (400 MHz, chloroform) δ=7.64-7.56 (m, 1H), 7.38-7.31 (m, 1H), 7.14-7.06 (m, 1H), 3.94-3.84 (m, 2H), 2.66-2.58 (m, 3H), 2.55-2.42 (m, 3H), 1.29-1.13 (m, 3H).

Example 5: Synthesis of 2-(3,4-dichlorophenyl)-1-ethyl-6-methyl-4-oxo-pyridine-3,5-dicarboxylic acid (Compound 2.010)

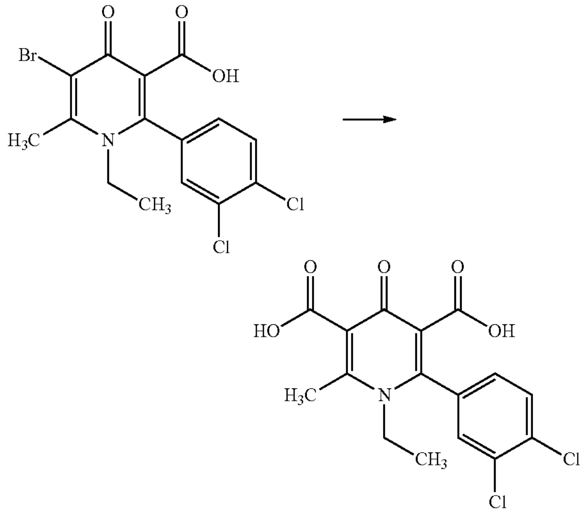

A cooled (−20° C.) suspension of 5-bromo-2-(3,4-dichlorophenyl)-1-ethyl-6-methyl-4-oxo-pyridine-3-carboxylic acid (0.100 g, 0.247 mmol) in anhydrous tetrahydrofuran (0.50 mL) and under nitrogen was added dropwise to a solution of isopropylmagnesium chloride lithium chloride complex (1.3 M in THF, 0.40 mL, 0.518 mmol) under nitrogen and at −20° C. The reaction mixture was stirred for 0.25 hours before being allowed to warm to −10° C. and stirred for 0.3 hours. The reaction mixture was re-cooled to −20° C. and isopropylmagnesium chloride lithium chloride complex solution (1.3 M in THF, 0.34 mL, 0.442 mmol) was added. The reaction mixture was stirred at −10° C. for 0.5 hours. A pellet of dry ice was allowed to sublime via cannular into the reaction mixture with stirring over 0.5 hours followed by addition of 2 small pellets of dry ice directly into the reaction mixture. The reaction mixture was stirred at room temperature for 0.5 hours. The reaction mixture was cooled to 0° C. and quenched by addition of saturated aqueous ammonium chloride solution (5 mL). The pH of the aqueous phase was adjusted to pH 3 by addition of aqueous hydrochloric acid (2M). The aqueous phase was extracted with dichloromethane (×3). The combined organic extracts were dried and evaporated to dryness under reduced pressure. The crude residue was purified by mass-directed HPLC to give 2-(3,4-dichlorophenyl)-1-ethyl-6-methyl-4-oxo-pyridine-3,5-dicarboxylic acid (0.019 g, 0.050 mmol, 20%) as a white solid.

$^1H$ NMR (400 MHz, DMSO-$d_6$) δ=7.84 (d, 1H), 7.82 (d, 1H), 7.48 (m, 1H), 3.88 (q, 2H), 2.74 (s, 3H), 1.10 (t, 3H).

TABLE 2

$^1H$ NMR Data for selected compounds of Table 1.

| Compound No. | Compound Name | Structure & $^1H$ NMR Data |
|---|---|---|
| 4.001 | methyl 2-(3,4-dichlorophenyl)-1-ethyl-6-methyl-4-oxo-5-vinyl-pyridine-3-carboxylate | 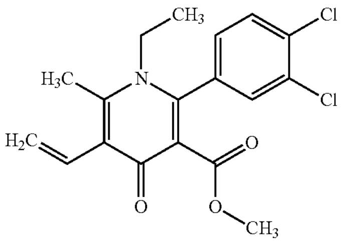 [SMILES: C=Cc1c(C)n(CC)c(-c2ccc(Cl)c(Cl)c2)c(C(=O)OC)c1=O] $^1H$ NMR (400 MHz, chloroform) δ = 7.55 (d, 1H), 7.50 (d, 1H), 7.24 (m, 1H), 6.63 (m, 1H), 5.99 (m, 1H), 5.62 (m, 1H), 3.80 (q, 2H), 3.57 (s, 3H), 2.54 (s, 3H), 1.15 (t, 3H). |
| 2.005 | 2-(3,4-dichlorophenyl)-1-ethyl-5-ethynyl-6-methyl-4-oxo-pyridine-3-carboxylic acid | 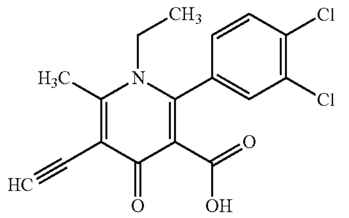 [SMILES: C#Cc1c(C)n(CC)c(-c2ccc(Cl)c(Cl)c2)c(C(=O)O)c1=O] $^1H$ NMR (400 MHz, acetonitrile-$d_3$) δ = 7.69 (d, 1H), 7.51 (d, 1H), 7.27 (m, 1H), 3.99 (s, 1H), 3.89 (q, 2H), 2.80 (s, 3H), 1.12 (t, 3H). |
| 2.001 | 2-(3,4-dichlorophenyl)-1-ethyl-6-methyl-4-oxo-5-vinyl-pyridine-3-carboxylic acid | 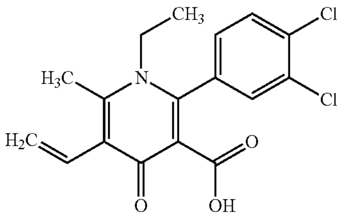 [SMILES: C=Cc1c(C)n(CC)c(-c2ccc(Cl)c(Cl)c2)c(C(=O)O)c1=O] $^1H$ NMR (400 MHz, chloroform) δ = 7.63-7.56 (m, 1H), 7.39-7.33 (m, 1H), 7.15-7.07 (m, 1H), 6.73-6.58 (m, 1H), 5.83-5.80 (m, 1H), 5.79-5.71 (m, 1H), 3.95-3.87 (m, 2H), 2.68-2.61 (m, 3H), 1.26-1.15 (m, 3H). |
| 2.008 | 5-acetyl-2-(3,4-dichlorophenyl)-1-ethyl-6-methyl-4-oxo-pyridine-3-carboxylic acid | 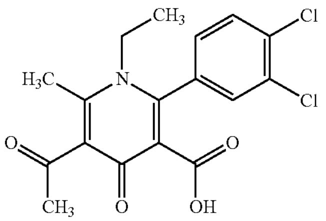 [SMILES: CCn1c(C)c(C(C)=O)c(=O)c(C(=O)O)c1-c1ccc(Cl)c(Cl)c1] $^1H$ NMR (400 MHz, chloroform) δ = 7.64-7.56 (m, 1H), 7.38-7.31 (m, 1H), 7.14-7.06 (m, 1H), 3.94-3.84 (m, 2H), 2.66-2.58 (m, 3H), 2.55-2.42 (m, 3H), 1.29-1.13 (m, 3H). |

TABLE 2-continued

| $^1H$ NMR Data for selected compounds of Table 1. | | |
|---|---|---|
| Compound No. | Compound Name | Structure & $^1H$ NMR Data |
| 2.010 | 2-(3,4-dichlorophenyl)-1-ethyl-6-methyl-4-oxo-pyridine-3,5-dicarboxylic acid | 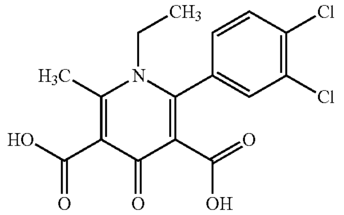 [SMILES: CCn1c(C)c(C(=O)O)c(=O)c(C(=O)O)c1-c1ccc(Cl)c(Cl)c1] $^1H$ NMR (400 MHz, DMSO-$d_6$) δ = 7.84 (d, 1H), 7.82 (d, 1H), 7.48 (m, 1H), 3.88 (q, 2H), 2.74 (s, 3H), 1.10 (t, 3H). |

BIOLOGICAL EXAMPLES

Seeds of a variety of test species are sown in standard soil in pots (*Amaranthus retoflexus* (AMARE), *Solanum nigrum* (SOLNI), *Setaria faberi* (SETFA), *Lolium perenne* (LOLPE), *Echinochloa crus-galli* (ECHCG), *Ipomoea hederacea* (IPOHE)). After 8 days cultivation under controlled conditions in a glasshouse (at 24° C./16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/ha unless otherwise stated. The test plants are then grown in a glasshouse under controlled conditions in a glasshouse (at 24° C./16° C., day/night; 14 hours light; 65% humidity) and watered twice daily. After 13 days the test is evaluated for the percentage damage caused to the plant. The biological activities are shown in the following table on a five-point scale (5=81-100%; 4=61-80%; 3=41-60%; 2=21-40%; 1=0-20%).

TABLE B1

| Post-emergence Test | | | | | | |
|---|---|---|---|---|---|---|
| Cpd No. | AMARE | SOLNI | SETFA | LOLPE | ECHCG | IPOHE |
| 4.001 | 1 | 1 | 4 | 4 | 1 | 2 |
| 2.005 | 5 | 4 | 5 | 5 | 3 | 4 |
| 2.001 | 1 | 1 | 4 | 4 | 2 | 4 |
| 2.008 | 2 | 2 | 3 | 5 | 3 | 2 |
| 2.010 | 2 | 2 | 1 | 1 | 1 | 2 |

TABLE B2

| Pre-emergence Test | | | | | | |
|---|---|---|---|---|---|---|
| Cpd No. | AMARE | SOLNI | SETFA | LOLPE | ECHCG | IPOHE |
| 4.001 | 1 | 1 | 1 | 1 | 1 | 1 |
| 2.005 | 1 | 4 | 4 | 1 | 1 | 4 |
| 2.001 | 1 | 1 | 4 | 4 | 3 | 3 |
| 2.008 | 1 | 3 | 5 | 4 | 3 | 3 |
| 2.010 | 1 | 3 | 1 | 2 | 1 | 1 |

The invention claimed is:

1. A compound of Formula (I):

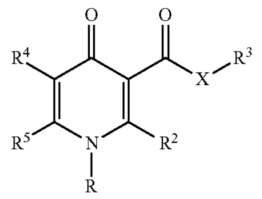

(I)

wherein

X is O, or S;

$R^1$ is $C_1$-$C_6$alkyl;

$R^2$ is phenyl, or heteroaryl, wherein the heteroaryl moiety is a 5- or 6-membered aromatic ring which comprises 1, 2, 3 or 4 heteroatoms individually selected from N, O and S, and wherein each phenyl or heteroaryl moiety is optionally substituted with 1, 2, 3, or 4 groups, which may be the same or different, represented by $R^7$;

$R^3$ is hydrogen, $C_1$-$C_6$alkyl, N,N-di($C_1$-$C_3$alkyl)amino, $C_1$-$C_6$haloalkyl, $C_3$-$C_6$cycloalkyl, $C_3$-$C_6$cycloalkyl$C_1$-$C_6$alkyl, $C_1$-$C_6$alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties are optionally substituted with 1, 2, 3 or 4 groups, which may be the same or different, represented by $R^8$, $R^4$ is $C_2$-$C_6$alkenyl, $C_2$-$C_6$alkynyl, $C_1$-$C_6$alkoxy$C_2$-$C_6$alkenyl, $C_2$-$C_6$alkenyloxy$C_1$-$C_6$alkyl, $C_1$-$C_6$alkylcarbonyl, or hydroxycarbonyl;

$R^5$ is halogen, $C_1$-$C_4$alkyl, $C_1$-$C_4$alkoxy, $C_1$-$C_4$haloalkyl, or $C_1$-$C_4$alkoxy$C_1$-$C_4$alkyl;

$R^7$ is halogen, $C_1$-$C_3$alkyl, or $C_1$-$C_3$alkoxy;

$R^8$ is halogen, cyano, $C_1$-$C_3$alkyl, or $C_1$-$C_3$alkoxy;

or a salt or an N-oxide thereof.

2. The compound according to claim 1, wherein $R^1$ is $C_1$-$C_4$alkyl.

3. The compound according to claim 1, wherein $R^2$ is phenyl or heteroaryl, wherein the heteroaryl moiety is a 5- or 6-membered aromatic ring which comprises 1, 2, or 3 heteroatoms individually selected from N, O and S, and wherein each phenyl or heteroaryl moiety is optionally substituted with 1, 2, or 3 groups, which may be the same or different, represented by $R^7$.

4. The compound according to claim 1, wherein $R^2$ is phenyl optionally substituted with 1 or 2 groups, which may be the same or different, represented by $R^7$.

5. The compound according to claim 1, wherein $R^3$ is hydrogen, $C_1$-$C_6$alkyl, N,N-di($C_1$-$C_3$alkyl)amino, $C_1$-$C_3$haloalkyl, $C_3$-$C_6$cycloalkyl, $C_3$-$C_6$cycloalkyl$C_1$-$C_3$alkyl, $C_1$-$C_4$alkoxy$C_1$-$C_2$alkyl, $C_2$-$C_3$alkenyl, $C_2$-$C_3$alkynyl, phenyl, or phenyl$C_1$-$C_2$alkyl, wherein the phenyl moieties are optionally substituted with 1, 2, or 3 groups, which may be the same or different, represented by $R^8$.

6. The compound according to claim 1, wherein $R^3$ is hydrogen, $C_1$-$C_4$alkyl, or N,N-di($C_1$-$C_3$alkyl)amino.

7. The compound according to claim 1, wherein $R^4$ is $C_2$-$C_6$alkenyl, $C_2$-$C_6$alkynyl, $C_1$-$C_6$alkylcarbonyl, or hydroxycarbonyl.

8. The compound according to claim 1, wherein $R^5$ is $C_1$-$C_4$alkyl.

9. The compound according to claim 1, wherein $R^7$ is halogen, methyl, ethyl, methoxy or ethoxy.

10. The compound according to claim 1, wherein X is O.

11. A herbicidal composition comprising the compound according to claim 1 and an agriculturally acceptable formulation adjuvant.

12. The herbicidal composition according to claim 11, further comprising at least one additional pesticide.

13. The herbicidal composition according to claim 12, wherein the at least one additional pesticide is a herbicide or herbicide safener.

14. A method of controlling unwanted plant growth, comprising applying the compound of Formula (I) as defined in claim 1, or a composition thereof, to the unwanted plants or to the locus thereof.

15. The compound according to claim 1, wherein $R^4$ is vinyl, ethynyl, acetyl, or carboxy.

16. The compound according to claim 1, wherein $R^1$, $R^2$ and $R^3$ are each as defined in claim 1; and $R^4$ and $R^5$ are each independently defined as:

| $R^4$ | $R^5$ |
|---|---|
| vinyl | methyl |
| vinyl | ethyl |
| vinyl | methoxmethyl |
| ethynyl | methyl |
| ethynyl | ethyl |
| ethynyl | methoxymethyl |
| acetyl | methyl |
| acetyl | ethyl |
| acetyl | methoxyethyl |
| carboxy | methyl |
| carboxy | ethyl |
| carboxy | methoxymethyl. |

17. A compound selected from:

methyl 2-(3,4-dichlorophenyl)-1-ethyl-6-methyl-4-oxo-5-vinyl-pyridine-3-carboxylate (Compound 4.001);

2-(3,4-dichlorophenyl)-1-ethyl-5-ethynyl-6-methyl-4-oxo-pyridine-3-carboxylic acid (Compound 2.005);

2-(3,4-dichlorophenyl)-1-ethyl-6-methyl-4-oxo-5-vinyl-pyridine-3-carboxylic acid (Compound 2.001);

5-acetyl-2-(3,4-dichlorophenyl)-1-ethyl-6-methyl-4-oxo-pyridine-3-carboxylic acid (Compound 2.008); and 2-(3,4-dichlorophenyl)-1-ethyl-6-methyl-4-oxo-pyridine-3,5-dicarboxylic acid (Compound 2.010).

18. A herbicidal composition comprising the compound according to claim 17 and an agriculturally acceptable formulation adjuvant.

19. The herbicidal composition according to claim 18, further comprising at least one additional pesticide.

20. The herbicidal composition according to claim 19, wherein the at least one additional pesticide is a herbicide or herbicide safener.

21. A method of controlling unwanted plant growth, comprising applying the compound according to claim 16, or a composition thereof, to the unwanted plants or to the locus thereof.

* * * * *